United States Patent [19]

Lautenschläger et al.

[11] 4,309,407
[45] Jan. 5, 1982

[54] ALKENYL-SUBSTITUTED THIENYLALKANECARBOXYLIC ACIDS AND DERIVATIVES THEREOF

[75] Inventors: Hans-Heiner Lautenschläger, Cologne; Hans Betzing, Kerpen-Horrem; Johannes Winkelmann, Cologne; Manfred Probst, Frechen, all of Fed. Rep. of Germany

[73] Assignee: A. Nattermann & Cie. GmbH, Cologne, Fed. Rep. of Germany

[21] Appl. No.: 206,077

[22] Filed: Nov. 12, 1980

[30] Foreign Application Priority Data

Nov. 20, 1979 [DE] Fed. Rep. of Germany ....... 2946810

[51] Int. Cl.³ ................. A61K 31/38; C07O 333/24
[52] U.S. Cl. ........................................ 424/275; 549/79
[58] Field of Search .......................... 549/74; 424/275

[56] References Cited

U.S. PATENT DOCUMENTS 3,691,202  9/1972  O'Mant ........................ 549/79

Primary Examiner—Alan Siegel
Attorney, Agent, or Firm—Burns, Doane, Swecker & Mathis

[57] ABSTRACT

The invention provides novel ω-(5-alkenylthien-2-yl)alkanecarboxylic acids and their functional derivatives having the formula

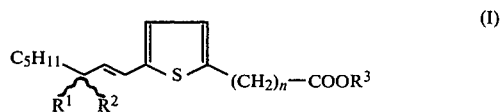

(I)

wherein n is an integer from 1 to 9, inclusive; $R^1$ is H and $R^2$ is —OH, or $R^1$ and $R^2$ together with the wavy lines represent a keto group; and $R^3$ is H, $C_1$-$C_6$ straight or branched-chain saturated hydrocarbon, or a pharmaceutically acceptable alkali cation. The 3-oxoalkenyl-substituted compounds of formula (I) are prepared by a Wittig-Horner reaction using a 2-oxoheptylphosphonic acid dialkyl ester and an aldehyde of the formula

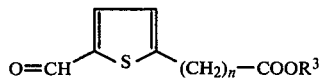

as starting materials, while the 3-hydroxyalkenyl-substituted compounds are obtained by reduction of the corresponding 3-oxoalkenyl compounds. The esters of formula (I) can also be readily converted to the corresponding acids and salts of formula (I).

The compounds of the invention have valuable anti-inflammatory, antipyretic and anti-arteriosclerotic properties, yet have low toxicity and do not irritate the gastric mucosa.

38 Claims, No Drawings

ALKENYL-SUBSTITUTED THIENYLALKANECARBOXYLIC ACIDS AND DERIVATIVES THEREOF

TECHNICAL FIELD:

The present invention is directed to novel alkenyl-substituted thienylalkanecarboxylic acids, their esters and their salts, to pharmaceutical compositions containing same, and to methods for the preparation and use of the subject compounds. The compounds of the invention display valuable anti-inflammatory, antipyretic and anti-arteriosclerotic properties, yet do not induce ulcers in the gastrointestinal tract.

BACKGROUND ART:

Many drugs produce disturbances in the gastrointestinal tract when administered orally. Thus, many effective analgesic, anti-inflammatory, or antipyretic (antiphlogistic) compounds are known to have the undesirable side effect of irritating the gastric mucosa, and, with long-term use, they may even cause gastric ulcers. This is true of acetylsalicyclic acid as well as of other analgesics [See, for example, Cooke, "Drugs and Gastric Damage" in *Drugs*, Volume 11, pp. 36–44 (1976), and Rainsford, "The Comparative Gastric Ulcerogenic Activities of Non-Steroid Anti-Inflammatory Drugs" in *Agents and Actions*, Volume 7, pp. 573–7 (1977)]. Consequently, it is apparent that a real need exists for new effective anti-inflammatory and antipyretic agents which will be devoid of the undesirable gastric side effects exhibited by the prior art compounds.

DISCLOSURE OF INVENTION:

Accordingly, the present invention has as an object the provision of a new group of anti-inflammatory and antipyretic agents, which agents are alkenyl-substituted thienylalkanecarboxylic acids and their functional derivatives having the formula

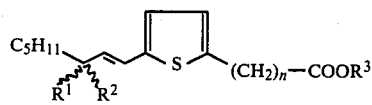
(I)

wherein n is an integer from 1 to 9, inclusive; $R^1$ is hydrogen and $R^2$ is hydroxy, or $R^1$ and $R^2$ taken together with the wavy lines represent a doubly bonded oxygen atom; and $R^3$ is hydrogen, a straight or branched-chain saturated hydrocarbon group of 1 to 6 carbon atoms, or a pharmaceutically acceptable alkali cation. The compounds of formula (I) have antiphlogistic properties and do not produce irritation of the gastric mucosa.

DETAILED DESCRIPTION OF THE INVENTION AND BEST MODE FOR CARRYING IT OUT

The new ω-(5-alkenylthien-2-yl)alkanecarboxylic acid derivatives of the present invention may be used in the form of the free acids, or as salts of pharmacologically compatible bases, or in the form of esters with common alcohols, as active ingredients in pharmaceutical compositions comprising one or more compounds of the invention in combination with a non-toxic pharmaceutically acceptable carrier therefor (i.e., any suitable excipient of diluent known in the art of pharmaceutical preparations). The alkyl esters of lower alkanols having 1 to 6 carbon atoms are particularly suitable for oral administration. The alkali salts of the invention can be any pharmaceutically acceptable basic salts of the subject acids, such as, for example, the alkali metal salts (e.g. sodium or potassium), alkaline earth metal/2 salts (e.g. calcium) and ammonium salts.

The carboxylic acid substituted on the 2-position of the thiophene ring may have up to 10 carbon atoms. It has been found that the compounds with a longer carboxylic acid ester are particularly effective, especially those in which n in formula (I) is 6 to 9. Also preferred are the compounds in which $R^1$ and $R^2$ together are a divalent oxygen atom, i.e. compounds with a keto group in the 3-position of the alkenyl radical. The following compounds of the invention are particularly preferred:

2-[5-(3-oxooct-1-enyl)thien-2-yl]acetic acid,
3-[5-(3-oxooct-1-enyl)thien-2-yl]propionic acid,
4-[5-(3-oxooct-1-enyl)thien-2-yl]butyric acid,
5-[5-(3-oxooct-1-enyl)thien-2-yl]valeric acid,
6-[5-(3-oxooct-1-enyl)thien-2-yl]hexanoic acid,
7-[5-(3-oxooct-1-enyl)thien-2-yl]heptanoic acid,
8-[5-(3-oxooct-1-enyl)thien-2-yl]octanoic acid,
9-[5-(3-oxooct-1-enyl)thien-2-yl]nonanoic acid,
10-[5-(3-oxooct-1-enyl)thien-2-yl]decanoic acid,
and the pharmaceutically acceptable salts and esters thereof.

Of the compounds of formula (I) containing hydroxy groups, i.e. compounds wherein $R^1$ is hydrogen and $R^2$ is hydroxy, the following substances may be mentioned as being particularly suitable:

7-[5-(3-hydroxyoct-1-enyl)thien-2-yl]heptanoic acid methyl ester,
8-[5-(3-hydroxyoct-1-enyl)thien-2-yl]octanoic acid methyl ester,
9-[5-(3-hydroxyoct-1-enyl)thien-2-yl]nonanoic acid methyl ester, and
10-[5-(3-hydroxyoct-1-enyl)thien-2-yl]decanoic acid methyl ester.

The alkenylthienyl alkanecarboxylic acids and their derivatives of the present invention can be prepared by a number of methods which are themselves known to one skilled in the art. One process according to the invention for preparing the compounds of formula (I) having a keto group in the alkene radical, i.e., the compounds wherein $R^1$ and $R^2$ together represent an oxygen atom, comprises reacting aldehydes of the general formula

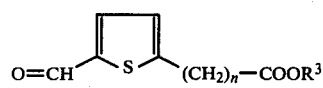
(II)

wherein n and $R^3$ are as defined hereinabove, in an organic solvent suitable for Wittig-Horner reactions, such as ethylene glycol dimethyl ether (1,2-dimethoxyethane) with a 2-oxoheptylphosphonic acid dialkyl ester, the alkyl portions of which each have 1 to 6 carbon atoms, e.g. 2-oxoheptylphosphonic acid dimethyl ester, in the presence of an auxiliary base which is suitable for such reactions, e.g. sodium hydride.

The compounds of formula (I) wherein $R^1$ and $R^2$ together represent an oxygen atom and $R^3$ is hydrogen can also be readily prepared from the corresponding esters of formula (I), i.e. the compounds wherein $R^3$ is an alkyl radical, e.g. by treatment, conveniently at room temperature, with alkaline hydroxides or alkaline carbonates (e.g. alkali metal hydroxides or alkali metal carbonates such as sodium hydroxide, potassium carbonate and the like) in water, alcohol solution, or alcohol-ether solution, to form the alkali salts of formula (I) where $R^3$ is an alkali cation, which can then be converted by subsequent addition of a mineral acid into the acids of the formula (I), i.e. the compounds in which $R^3$ is a hydrogen atom.

Alternatively, the salts can be obtained by treating the corresponding acids of formula (I), i.e. the compounds wherein $R^3$ is a hydrogen atom, with alkaline hydroxides or alkaline carbonates in water or alcohol/water solution, and then recovering the salts by subsequent concentration of the solutions.

The invention further provides a process for preparing the compounds of formula (I) wherein $R^1$ is a hydrogen atom and $R^2$ is a hydroxy group, by reduction of the corresponding keto compounds, in a suitable solvent medium, e.g. an alcohol/water solvent system, using an appropriate reducing agent, such as sodium borohydride, to reduce the keto group. Other suitable reducing agents for reducing a keto group to a hydroxy group without adversely affecting the remainder of the molecule are known in the art and will be apparent to the skilled organic chemist. Alternatively, the acids and salts of formula (I) wherein $R^1$ is H and $R^2$ is OH can be prepared from the corresponding esters of formula (I) in the same way as described above for the acids and salts where $R^1$ and $R^2$ are keto.

The process of the present invention which is particularly suited for preparing the new thiophene derivatives of formula (I) may additionally be illustrated by the following equations, in which starting materials comprising compounds of formula (II) are reacted with a 2-oxoheptenyl compound by a Wittig-Horner reaction:

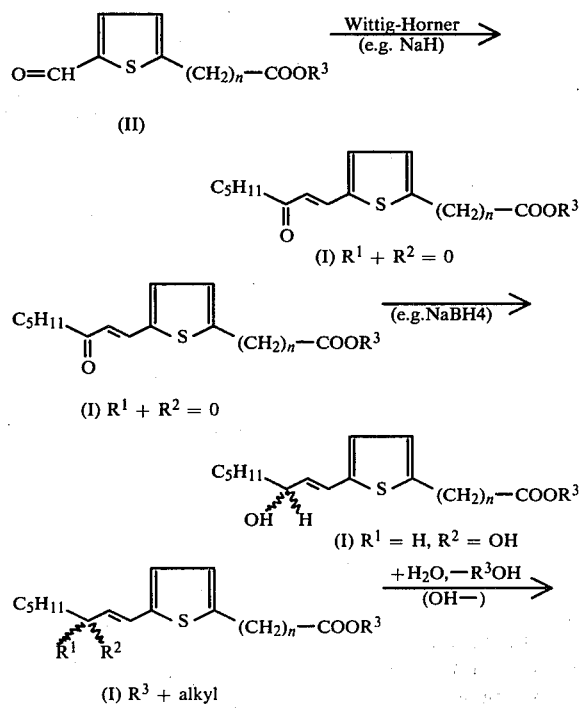

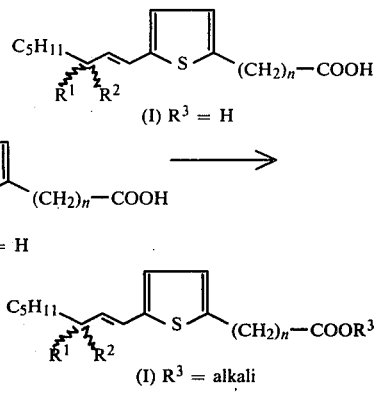

Suitable starting materials of formula (II) for use in the Wittig-Horner reaction of the present invention are, for example, esters or alkali salts of the following acids:
2-(5-formylthien-2-yl)acetic acid,
3-(5-formylthien-2-yl)propionic acid,
4-(5-formylthien-2-yl)butyric acid,
5-(5-formylthien-2-yl)valeric acid,
6-(5-formylthien-2-yl)hexanoic acid,
7-(5-formylthien-2-yl)heptanoic acid,
8-(5-formylthien-2-yl)octanoic acid,
9-(5-formylthien-2-yl)nonanoic acid,
10-(5-formylthien-2-yl)decanoic acid.

The new thiophene derivatives of formula (I) display valuable pharmacological properties at very low doses, properties such as antiphlogistic (anti-inflammatory/antipyretic) and anti-arteriosclerotic action. They additionally display antiulcerogenic properties and thus excellent gastric tolerance as well as low toxicity. Accordingly, the compounds of formula (I) are particularly useful in the treatment of inflammation and of arteriosclerotic disorders, while being at the same time benign in their gastrointestinal properties.

The new compounds of formula (I) may be administered, e.g., orally, by injection, topically, or rectally, in suitable formulations which may be solid, semi-solid or liquid, in the form of suspensions or solutions. Examples of such formulations are tablets, powders, capsules, granules, pastilles, ampules, syrups, suppositories, ointments and foams.

The compounds of the invention are conveniently administered to warm-blooded animals by combining the selected compound or compounds of the invention with any suitable nontoxic pharmaceutically acceptable inert carrier. Such carriers are well known to those skilled in the art of pharmaceutical formulations. Thus, for example, in a typical preparation for oral administration, e.g., tablet or capsule, any one of the compounds of the instant invention is combined in a anti-inflammatory, antipyretic or anti-arteriosclerotic effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes.

Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, any one of the compounds of the instant invention is combined with a typical vehicle such as triacetin, such that the active ingredient is present in an anti-inflammatory effective amount.

Naturally, the therapeutic dosage range for the compounds of the instant invention will vary with the size and needs of the patient, the particular compound employed and the condition for which the compound is administered. However, generally speaking, the dosage range are 50 mg to 5 g, administered once or several times daily. Preferably, 100 to 500 mg of compound are administered as a unit dose, two or three times daily.

The preparation of compounds of the present invention will be illustrated in more detail by the following examples. These examples are to be construed as merely illustrative and in no way limitative of the remainder of the specification and claims, as many modifications in materials and methods will be apparent to those skilled in the art. The aldehydes of formula (II) which were used as the starting materials in the examples which follow were prepared from the corresponding ω-(2-thienyl)alkanoic acid esters according to methods known from the literature [the Vilsmeyer synthesis; see, e.g., B. P. Fabrichnyi et al., Zhur. Obshchey Khim., 28, 2520–30 (1958)]. The melting points given were measured with a Buechi 510 melting point determination apparatus, and are not corrected. The ir spectra were recorded with Perkin-Elmer 257 equipment.

EXAMPLE 1

Preparation of 5-[5-(3-oxooct-1-enyl)thien-2-yl]valeric acid methyl ester.

1.6 G of 80% sodium hydride in mineral oil suspension were washed with n-pentane and suspended in 260 ml of 1,2-dimethoxyethane; 11.1 g of 2-oxoheptylphosphonic acid dimethyl ester dissolved in 110 ml of 1,2-dimethoxyethane were added to this suspension dropwise. The reaction mixture was stirred for 1.5 hours at 20° C., then was mixed with 10.3 g of 5-(2-formylthien-2-yl)valeric acid methyl ester dissolved in a small amount of 1,2-dimethoxyethane, and then again stirred for 1.5 hours at 25° C. At the end of that time, the mixture was acidified to pH 6 with dilute sulfuric acid and the reaction mixture was concentrated under vacuum. The residue was dissolved in dichloromethane, the dichloromethane solution was dried over sodium sulfate, the solvent was removed by distillation, and the residue was purified by column chromatography (silica gel, using toluene and ethyl acetate as eluants). The product was obtained as an oil, 7.1 g (48% yield); ir (film): 1740, 1665, 1600 cm$^{-1}$.

EXAMPLE 2

Preparation of 6-[5-(3-oxooct-1-enyl)thien-2-yl]hexanoic acid methyl ester.

2.4 G of 80% sodium hydride in mineral oil suspension was washed with n-pentane and suspended in 400 ml of 1,2-dimethoxyethane; 16 g of 2-oxoheptylphosphonic acid dimethyl ester dissolved in 150 ml of 1,2-dimethoxyethane were added to this suspension dropwise. The reaction mixture was stirred 1.5 hours at 20° C., then was mixed with 15.7 g of 6-(5-formylthien-2-yl)hexanoic acid methyl ester dissolved in approximately 100 ml of 1,2-dimethoxyethane, and then again stirred for 1.5 hours at 25° C. Then, the mixture was acidified to pH 6 with diluted sulfuric acid, and the reaction mixture was concentrated under vacuum. The residue was dissolved in dichloromethane, the dichloromethane solution was dried over sodium sulfate, the solvent was removed by distillation, and the residue was purified by column chromatography (silica gel, using hexane and ethyl acetate as eluants). The product was obtained as an oil, 4.4 g (20% yield); ir (film): 1730, 1660, 1605 cm$^{-1}$.

EXAMPLE 3

Preparation of 7-[5-(3-oxooct-1-enyl)thien-2-yl]heptanoic acid methyl ester.

1.52 G of 80% sodium hydride in mineral oil suspension was washed with n-pentane and suspended in 300 ml of 1,2-dimethoxyethane; 10.5 g of 2-oxoheptylphosphonic acid dimethyl ester dissolved in 100 ml of 1,2-dimethoxyethane were added to this suspension dropwise. The reaction mixture was stirred 1.5 hours at 20° C., then was mixed with 10.9 g of 7-(5-formylthien-2-yl)heptanoic acid methyl ester dissolved in a small amount of 1,2-dimethoxymethane, and then again stirred for 1.5 hours at 25° C. At the end of that time, the mixture was acidified to pH with dilute sulfuric acid and the reaction mixture was concentrated under vacuum. The residue was dissolved in dichloromethane, the dichloromethane solution was dried over sodium sulfate, the solvent was removed by distillation, and the residue was purified by column chromatography (silica gel, using petroleum ether and ethyl acetate as eluants). The product was obtained as an oil, 7.8 g (52% yield); ir (film): 1740, 1685 (shoulder), 1660, 1600 cm$^{-1}$.

EXAMPLE 4

Preparation of 8-[5-(3-oxooct-1-enyl)thien-2-yl]octanoic acid methyl ester.

1.35 G of 80% sodium hydride in mineral oil suspension was washed with n-pentane and suspended in 220 ml of 1,2-dimethoxyethane; then 9.1 g of 2-oxoheptylphosphonic acid dimethyl ester dissolved in 90 ml of 1,2-dimethoxyethane was added to the suspension dropwise. The reaction mixture was stirred for 1.5 hours at 20° C., then 9.8 g of 8-(5-formylthien-2-yl)octanoic acid methyl ester dissolved in 100 ml 1,2-dimethoxyethane was added. Stirring was resumed for 1.5 hours at 25° C. Then, the reaction mixture was acidified to pH 6 with dilute sulfuric acid and concentrated under vacuum. The residue was dissolved in dichloromethane, the dichloromethane solution was dried over sodium sulfate and the solvent was removed by distillation. The resultant residue was purified by column chromatography (silica gel, using hexane and ethyl acetate as eluants). The product was obtained as an oil, 5.7 g (40% yield); ir (film): 1740, 1680 (shoulder), 1660, and 1595 cm$^{-1}$.

EXAMPLE 5

Preparation of 9-[5-(3-oxooct-1-enyl)thien-2-yl]nonanoic acid methyl ester.

3.3 G of 80% sodium hydride in mineral oil suspension was washed with n-pentane and suspended in 600 ml of 1,2-dimethoxyethane; 23.2 g of 2-oxoheptylphosphonic acid dimethyl ester dissolved in 200 ml of 1,2-dimethoxyethane was then added to the suspension dropwise. The mixture was stirred for 1.5 hours at 20° C., then was mixed with 26.8 g of 9-(5-formylthien-2-yl)nonanoic acid methyl ester dissolved in a small amount of 1,2-dimethoxyethane. The reaction mixture was again stirred for 1.5 hours at 25° C. Then, the mixture was acidified to pH 6 with dilute sulfuric acid and concentrated under vacuum. The residue was dissolved in dichloromethane, the dichloromethane solution was dried over sodium sulfate, the solvent was removed by distillation and the residue was purified by column chromatography (silica gel, using hexane and ethyl acetate as eluants). 18.2 G (51% yield) of product, with melting point 29°–31° C., was obtained; ir (film): 1740, 1685 (shoulder), 1660, and 1600 cm$^{-1}$.

EXAMPLE 6

Preparation of 10-[5-(3-oxooct-1-enyl)thien-2-yl]decanoic acid methyl ester.

1.45 G of 80% sodium hydride in mineral oil suspension was washed with n-pentane and suspended in 250 ml of 1,2-dimethoxyethane; then, 9.7 g of 2-oxoheptylphosphonic acid dimethyl ester dissolved in 100 ml of 1,2-dimethoxyethane was added dropwise to than suspension. The mixture was stirred for 1.5 hours at 20° C., then 11.2 g of 10-(5-formylthien-2-yl)decanoic acid methyl ester dissolved in a small amount of 1,2-dimethoxyethane was added. Stirring was resumed for an additional 1.5 hours at 25° C. Then, the mixture was acidified to pH 6 with dilute sulfuric acid and concentrated under vacuum. The residue was dissolved in dichloromethane, the dichloromethane solution was dried over sodium sulfate, the solvent was removed by distillation, and the residue was purified by column chromatography (silica gel, using hexane and ethyl acetate as eluants). There were thus obtained 8.6 g (58% yield) of the desired product, melting at 45°–47° C.; ir (in KBr): 1740, 1690 (shoulder), 1660, and 1600 cm$^{-1}$.

The $C_2$ to $C_6$ alkyl esters are prepared analogously to the methyl esters of Examples 1 through 6, e.g.:

7-[5-(3-oxooct-1-enyl)thien-2-yl]heptanoic acid ethyl ester, an oil; ir (film): 1740, 1670, and 1600 cm$^{-1}$;

2-[5-(3-oxooct-1-enyl)thien-2-yl]acetic acid hexyl ester, an oil; ir (film): 1740, 1670, and 1605 cm$^{-1}$.

EXAMPLE 7

Preparation of 2-[5-(3-oxooct-1-enyl)thien-2-yl]acetic acid.

3.5 G of 2-[5-(3-oxooct-1-enyl)thien-2-yl]acetic acid hexyl ester was dissolved in 20 ml of ethanol; then, a solution of 0.6 g of potassium hydroxide in 10 ml ethanol was added portionwise over a period of 4 hours. The resultant solution was stirred for an additional 4 hours, then was diluted with water. The water solution was extracted several times with ether, and the ether phases were discarded. The water solution was adjusted to pH 5.5 to 6 with dilute hydrochloric acid and extracted with ether, and the ether phase was washed with water, dried over sodium sulfate, and concentrated under vacuum. The residue was purified by column chromatography (silica gel, using benzene and ethyl acetate as eluants). There were thus obtained 1.2 g (45% yield) of the desired product, melting at 51° C.

EXAMPLE 8

Preparation of 7-[5-(3-oxooct-1-enyl)thien-2-yl]heptanoic acid.

9 G of 7-[5-(3-oxooct-1-enyl)thien-2-yl]heptanoic acid methyl ester was dissolved in 25 ml of ethanol; then, a solution of 1.6 g of potassium hydroxide in 25 ml of ethanol was added portionwise over a period of 4 hours. The resultant solution was stirred for an additional 4 hours, then was diluted with water. The water solution was extracted several times with ether, and the ether phases were discarded. The water solution was adjusted to pH 5.5 to 6 with dilute hydrochloric acid and extracted with ether, and the ether phase was washed with water, dried over sodium sulfate, and concentrated under vacuum. The residue was purified by column chromatography (silica gel, using toluene and ethyl acetate as eluants). The yield of desired product was 6.5 g (74%), with melting point 69°–70° C., ir (in KBr): 1725 and 1620 cm$^{-1}$.

The following acids are prepared by means analogous to those used to prepare the acids of Examples 7 and 8:
3-[5-(3-oxooct-1-enyl)thien-2-yl]propionic acid,
4-[5-(3-oxooct-1-enyl)thien-2-yl]butyric acid,
5-[5-(3-oxooct-1-enyl)thien-2-yl]valeric acid,
6-[5-(3-oxooct-1-enyl)thien-2-yl]hexanoic acid,
8-[5-(3-oxooct-1-enyl)thien-2-yl]octanoic acid,
9-[5-(3-oxooct-1-enyl)thien-2-yl]nonanoic acid, and
10-[5-(3-oxooct-1-enyl)thien-2-yl]decanoic acid.

EXAMPLE 9

Preparation of 7-[5-(3-oxooct-1-enyl)thien-2-yl]heptanoic acid, sodium salt.

3.4 G of 7-[5-(3-oxooct-1-enyl)thien-2-yl]heptanoic acid were dissolved in ethanol and titrated with alcoholic sodium hydroxide. The mixture was concentrated to dryness under vacuum, and the solid residue was pulverized. The yield was 3.6 g (100%); ir (in KBr): 1655 and 1565 cm$^{-1}$.

The following sodium salts are prepared by means analogous to those used in the preceding paragraph:
2-5-(3-oxooct-1-enyl)thien-2-yl]acetic acid, sodium salt;
3-[5-(3-oxooct-1-yl]propionic acid, sodium salt;
4-[5-(3-oxooct-1-enyl)thien-2-yl]butyric acid, sodium salt;
5-[5-(3-oxooct-1-enyl)thien-2-yl]valeric acid, sodium salt;
6[5-(3-oxooct-1-enyl)thien-2-yl]hexanoic acid, sodium salt;
8-[5-(3-oxooct-1-enyl)thien-2-yl]octanoic acid, sodium salt;
9-[5-(3-oxooct-1-enyl)thien-2-yl]nonanoic acid, sodium salt; and 10-[5-(3oxooct-1-enyl)thien-2-yl]decanoic acid, sodium salt.

Other alkali metal salts, e.g., the potassium salts, can be prepared in like manner, as can yet other alkali salts such as ammonium and alkaline earth metal/2 salts.

EXAMPLE 10

Preparation of 8-[5-(3-hydroxyoct-1-enyl)thien-2-yl]octanoic acid methyl ester.

1 G of 8-[5-(3-oxooct-1-enyl)thien-2-yl]octanoic acid methyl ester was dissolved in 25 ml of methanol and the solution was cooled to about 0° C. Under vigorous stirring, 0.9 g of sodium borohydride was added and the reaction mixture was warmed slowly to room temperature after a period of 30 minutes. After about 1 hour, the reaction mixture was diluted with water, adjusted to a pH of 5.5 to 6 with dilute hydrochloric acid and extracted with ether. The ether phase was washed with water, dried over sodium sulfate, and then concentrated to dryness under vacuum. The residue was purified by column chromatography (silica gel, using petroleum ether and ethyl acetate as eluants). The product was obtained as 0.9 g of an oil (90% yield); ir (film): 3450 (OH), 1740 (C=O), and 1645 cm$^{-1}$ (C=C).

Other esters of the corresponding hydroxy compounds are produced by reduction, by means analogous to those used for the hydroxy ester of the preceding paragraph, for example;

7-[5-(3-hydroxyoct-1-enyl)thien-2-yl]heptanoic acid, methyl ester (an oil),

9-[5-(3-hydroxyoct-1-enyl)thien-2-yl]nonanoic acid, methyl ester (an oil), and

10-[5-(3-hydroxyoct-1-enyl)thien-2-yl]decanoic acid, methyl ester (an oil).

The following examples illustrate compositions containing compounds of formula (I) and excipients or auxiliary materials which are in common use in pharmaceutical practice, which compositions can be used as pharmaceuticals, e.g., in the treatment of inflammation or arteriosclerosis.

EXAMPLE 11

Tablets..

A mixture of 50 g of 9-[5-(3-oxooct-1-enyl)thien-2-yl]nonanoic acid methyl ester, 50 g of lactose, 16 g of cornstarch, 2 g of cellulose powder, and 2 g of magnesium stearate was pressed into tablets, such that each tablet contained 50 mg of the active substance.

EXAMPLE 12

Coated Tablets.

Tablets were pressed as per the previous example, and were thereafter coated with a coating comprising sugar, cornstarch, talc, and tragacanth.

EXAMPLE 13

Ampules.

100 G of 7-[5-(3-oxooct-1-enyl)thien-2-yl]heptanoic acid, sodium salt, were dissolved in a mixture of 9.5 liter of twice-distilled water and 0.5 liter of ethylene glycol, filtered sterile, and 10 ml aliquots of the resulting solution were charged under sterile conditions into ampules which were then melted closed.

In order to demonstrate the therapeutic advance provided by the present invention, a representative compound, namely 9-[5-(3-oxooct-1-enyl)thien-2-yl]nonanoic acid methyl ester (the compound of Example 5), was tested in a series of pharmacological comparison tests using known standard testing methods, with indomethacin being used as the known comparison substance.

The results of these four tests are given in the following tabulation.

1. Rat Paw Edema Test [methodology as per Hillebrecht, Arzneim.-Forsch (4), 607 (1954)].

|  | Compound of Example 5 | | Indomethacin | |
|---|---|---|---|---|
| Dose, mg/kg per os | 0.1 | .0 | 3.2 | 5.6 |
| Inhibiting effect (%) | −26 | −38 | −25 | −45 |

2. Granuloma Test (Cotton Pellet Test) [methodology as per R. Meier et al., Experientia 6, 469 (1950)]

|  | Compound of Example 5 | | Indomethacin | |
|---|---|---|---|---|
| Rat dose, mg/kg per os | 0.1 | 1.0 | 0.1 | 3.2 |
| Decrease in weight of granuloma (%) | −24 | −13 | −21 | −27 |

3. Adjuvans Arthritis Test, Rat, p.o. [methodology as per C. N. Pearson, Proc. Soc. Exp. Biol. 91, 95–101 (1956)].

|  | Compound of Example 5 | Indomethacin |
|---|---|---|
| Dose, mg/kg p.o. | 0.1 | 0.1 |
| Inhibiting effect (%) | | |
| 14th day p.i. | −28 | −29 |
| 17th day p.i. | −35 | −37 |

(p.i. = post infection)

4. Ulcer-Inducing Effect on rats [methodology according to W. J. R. Whittle, Brit. J. Pharmacol. 55, 242–3 (1975)].

|  | Compound of Example 5 | | | Indomethacin | | |
|---|---|---|---|---|---|---|
| Dose, mg/kg per os | 1 | 10 | 100 | 3.2 | 5.6 | 7.5 |
| Effect | 0 | 0 | 0 | ++ | +++ | +++ |

Key:
0 = no ulcer induction
+ = moderate ulcer induction
++ = severe ulcer induction
+++ = very sever ulcer induction These comparative tests show the favorable antiphlogistic action and absence of ulcer inducing effects of the representative compound of the present invention against a prior art compound which has hitherto been regarded as very effective but which causes ulcers even at low doses.

Similar results were obtained in subjecting other of the compounds of the invention to the same pharmacological tests; those compounds also showed favorable action in the Rat Paw Edema Test, the Granuloma Test, and the Adjuvans Arthritis Test, as against the reference compound, and no ulcer irritation was detectable in rat tests.

From the foregoing description, one of ordinary skill in the art can easily ascertain the essential characteristics of the instant invention, and without departing from the spirit and scope thereof, can make various changes and/or modifications of the instant invention to adapt it

What is claimed is:

1. A compound of the formula

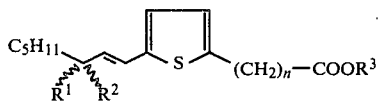

wherein n is an integer from 1 to 9, inclusive; $R^1$ is a hydrogen atom and $R^2$ is a hydroxy group, or $R^1$ and $R^2$ together with the wavy lines represent a doubly bonded oxygen atom; and $R^3$ is a hydrogen atom, a straight or branched-chain saturated hydrocarbon group containing 1 to 6 carbon atoms, or a pharmaceutically acceptable alkali cation.

2. A compound according to claim 1 wherein n is 7, 8 or 9.

3. A compound according to claim 1 wherein $R^1$ and $R^2$ together with the wavy lines represent a doubly bonded oxygen atom.

4. A compound according to claim 1, 2 or 3 wherein $R^3$ is a hydrogen atom.

5. A compound according to claim 1, 2 or 3 wherein $R^3$ is a pharmaceutically acceptable alkali cation.

6. A compound according to claim 5 wherein $R^3$ is an alkali metal cation.

7. A compound according to claim 1, 2 or 3 wherein $R^3$ is a straight or branched-chain saturated hydrocarbon group containing 1 to 6 carbon atoms.

8. A compound according to claim 7 wherein $R^3$ is a methyl radical.

9. A compound according to claim 7 wherein $R^3$ is a $C_2$-$C_6$ alkyl radical.

10. A compound according to claim 1 which is 2-[5-(3-oxooct-1-enyl)thien-2-yl]acetic acid or a pharmaceutically acceptable salt or ester thereof.

11. A compound according to claim 1 which is 3-[5-(3-oxooct-1-enyl)thien-2-yl]propionic acid or a pharmaceutically acceptable salt or ester thereof.

12. A compound according to claim 1 which is 4-[5-(3-oxooct-1-enyl)thien-2-yl]butyric acid or a pharmaceutically acceptable salt or ester thereof.

13. A compound according to claim 1 which is 5-[5-(3-oxooct-1-enyl)thien-2-yl]valeric acid or a pharmaceutically acceptable salt or ester thereof.

14. A compound according to claim 1 which is 6-[5-(3-oxooct-1-enyl)thien-2-yl]hexanoic acid or a pharmaceutically acceptable salt or ester thereof.

15. A compound according to claim 1 which is 7-[5-(3-oxooct-1-enyl)thien-2-yl]heptanoic acid or a pharmaceutically acceptable salt or ester thereof.

16. A compound according to claim 1 which is 8-[5-(3-oxooct-1-enyl)thien-2-yl]octanoic acid or a pharmaceutically acceptable salt or ester thereof.

17. A compound according to claim 1 which is 9-[5-(3-oxooct-1-yl)thien-2-yl]nonionic acid or a pharmaceutically acceptable salt or ester thereof.

18. A compound according to claim 1 which is 10-[5-(3-oxooct-1-enyl)thien-2-yl]decanoic acid or a pharmaceutically acceptable salt or ester thereof.

19. The compound according to claim 1 which is 7-[5-(3-hydroxyoct-1-enyl)thien-2-yl]heptanoic acid methyl ester.

20. The compound according to claim 1 which is 8-[5-(3-hydroxyoct-1-enyl)thien-2-yl]octanoic acid methyl ester.

21. The compound according to claim 1 which is 9-[5-(3-hydroxyoct-1-enyl)thien-2-yl]nonanoic acid methyl ester.

22. The compound according to claim 1 which is 10-[5-(3-hydroxyoct-1-enyl)thien-2-yl]decanoic acid methyl ester.

23. The compound according to claim 1 which is 5-[5-(3-oxooct-1-enyl)thien-2-yl]valeric acid methyl ester.

24. The compound according to claim 1 which is 6-[5-(3-oxooct-1-enyl)thien-2-yl]hexanoic acid methyl ester.

25. The compound according to claim 1 which is 7-[5-(3-oxooct-1-enyl)thien-2-yl]heptanoic acid methyl ester.

26. The compound according to claim 1 which is 8-[5-(3-oxooct-1-enyl)thien-2-yl]octanoic acid methyl ester.

27. The compound according to claim 1 which is 9-[5-(3-oxooct-1-enyl)thien-2-yl]nonanoic acid methyl ester.

28. The compound according to claim 1 which is 10-[5-(3-oxooct-1-enyl)thien-2-yl]decanoic acid methyl ester.

29. A pharmaceutical composition for the treatment of inflammation comprising an effective anti-inflammatory amount of a compound of formula (I) as defined by claim 1, and a non-toxic, pharmaceutically acceptable carrier therefor.

30. A pharmaceutical composition for the reduction of fever comprising an effective antipyretic amount of a compound of formula (I) as defined by claim 1, and a non-toxic pharmaceutically acceptable carrier therefor.

31. A pharmaceutical composition for the treatment of arteriosclerotic disorders comprising an effective anti-arteriosclerotic amount of a compound of formula (I) as defined by claim 1, and a non-toxic pharmaceutically acceptable carrier therefor.

32. A pharmaceutical composition according to claim 29, 30, or 31 wherein the compound of formula (I) is selected from the group consisting of:
2-[5-(3-oxooct-1-enyl)thien-2-yl]acetic acid,
3[5-(3-oxooct-1-enyl)thien-2-yl]propionic acid,
4-[5-(3-oxooct-1-enyl)thien-2-yl]butyric acid,
5-[5-(3-oxooct-1-enyl)thien-2-yl]valeric acid,
6-[5-(3-oxooct-1-enyl)thien-2-yl]hexanoic acid,
7-[5-(3-oxooct-1-enyl)thien-2-yl]heptanoic acid,
8-[5-(3-oxooct-1-enyl)thien-2-yl]octanoic acid,
9-[5-(3-oxooct-1-enyl)thien-2-yl]nonanoic acid, and
10-[5-(3-oxooct-1-enyl)thien-2-yl]decanoic acid,
and the pharmaceutically acceptable salts and esters thereof.

33. A pharmaceutical composition of claim 29, 30 or 31 wherein the compound of formula (I) is selected from the group consisting of:
7-[5-(3-hydroxyoct-1-enyl)thien-2-yl]heptanoic acid methyl ester,
8-[5-(3-hydroxyoct-1-enyl)thien-2-yl]octanoic acid methyl ester,
9-[5-(3-hydroxyoct-1-enyl)thien-2-yl]nonanoic acid methyl ester, and
10-[5-(3-hydroxyoct-1-enyl)thien-2-yl]decanoic acid methyl ester.

34. A pharmaceutical composition according to claim 29, 30 or 31 wherein the compound of formula (I) is selected from the group consisting of:

5-[5-(3-oxooct-1-enyl)thien-2-yl]valeric acid methyl ester,

6-[5-(3-oxooct-1-enyl)thien-2-yl]hexanoic acid methyl ester,

7-[5-(3-oxooct-1-enyl)thien-2-yl]heptanoic acid methyl ester,

8-[5-(3-oxooct-1-enyl)thien-2-yl]octanoic acid methyl ester,

9-[5-(3-oxooct-1-enyl)thien-2-yl]nonanoic acid methyl ester, and

10-[5-(3-oxooct-1-enyl)thien-2-yl]decanoic acid methyl ester.

35. A pharmaceutical composition according to claim 34 wherein the compound of formula (I) is 9-[5-(3-oxooct-1-enyl)thien-2-yl]nonanoic acid methyl ester.

36. A method of treating inflammation in or on a mammal which comprises administering thereto an effective anti-inflammatory amount of a compound of formula (I) as defined by claim 1, in combination with a non-toxic pharmaceutically acceptable carrier therefor.

37. A method of reducing fever in a mammal which comprises administering thereto an effective antipyretic amount of a compound of formula (I) as defined by claim 1, in combination with a non-toxic pharmaceutically acceptable carrier therefor.

38. A method of treating an arteriosclerotic disorder in a mammal which comprises administering thereto an effective anti-arteriosclerotic amount of a compound of formula (I) as defined by claim 1, in combination with a non-toxic pharmaceutically acceptable carrier therefor.

* * * * *